US007405327B2

(12) United States Patent
Haese et al.

(10) Patent No.: US 7,405,327 B2
(45) Date of Patent: Jul. 29, 2008

(54) METHOD FOR THE CONTINUOUS PRODUCTION OF AN AMINE

(75) Inventors: Frank Haese, Bollingstedt (DE); Arnd Bottcher, Kuantan (MY); Bernd Stein, Alsbach-Hähnlein (DE); Wolfgang Reif, Frankenthal (DE); Johann-Peter Melder, Böhl-Iggelheim (DE); Karl-Heinz Roβ, Grünstadt (DE); Heinz Rutter, Kapellen (BE); Shelue Liang, Nanjing (CN); Stefan Rittinger, Kuantan (MY)

(73) Assignee: BASF Aktiengesellschaft, Ludwigshafen (DE)

( * ) Notice: Subject to any disclaimer, the term of this patent is extended or adjusted under 35 U.S.C. 154(b) by 68 days.

(21) Appl. No.: 11/596,292

(22) PCT Filed: May 4, 2005

(86) PCT No.: PCT/EP2005/004817

§ 371 (c)(1), (2), (4) Date: Nov. 13, 2006

(87) PCT Pub. No.: WO2005/110969

PCT Pub. Date: Nov. 24, 2005

(65) Prior Publication Data

US 2007/0232833 A1 Oct. 4, 2007

(30) Foreign Application Priority Data

May 13, 2004 (DE) ....................... 10 2004 023 529

(51) Int. Cl.
*C07C 209/26* (2006.01)

(52) U.S. Cl. ........................ 564/472; 564/446; 564/473

(58) Field of Classification Search ....................... None
See application file for complete search history.

(56) References Cited

U.S. PATENT DOCUMENTS

| | | | |
|---|---|---|---|
| 3,275,554 | A | 9/1966 | Wagenaar |
| 4,310,697 | A | 1/1982 | Cheminal et al. |
| 4,739,051 | A | 4/1988 | Schroeder et al. |
| 4,910,304 | A | 3/1990 | Fischer et al. |
| 5,290,932 | A | 3/1994 | Dingerdissen et al. |
| 5,847,131 | A | 12/1998 | Simon et al. |
| 5,917,039 | A | 6/1999 | Simon et al. |
| 6,111,100 | A | 8/2000 | Riechers et al. |

FOREIGN PATENT DOCUMENTS

| | | | |
|---|---|---|---|
| DE | 2125039 | | 12/1971 |
| DE | 3611230 | A1 | 10/1987 |
| DE | 19859776 | A1 | 6/2000 |
| DE | 10053386 | A1 | 5/2001 |
| EP | 0137478 | A2 | 4/1985 |
| EP | 0167872 | A2 | 1/1986 |
| EP | 0227904 | A1 | 7/1987 |
| EP | 0257443 | A1 | 3/1988 |
| EP | 0514692 | A2 | 11/1992 |
| EP | 0542039 | A1 | 5/1993 |
| EP | 0816350 | A1 | 1/1998 |
| EP | 0863140 | A1 | 9/1998 |
| EP | 1020455 | A1 | 7/2000 |
| HU | 212713 | A | 2/1997 |
| JP | 02111765 | A | 4/1990 |

*Primary Examiner*—Brian J Davis
(74) *Attorney, Agent, or Firm*—Connolly Bove Lodge & Hutz LLP

(57) ABSTRACT

Process for the continuous preparation of an amine by reaction of a primary or secondary alcohol, aldehyde and/or ketone with hydrogen and a nitrogen compound selected from the group consisting of ammonia, primary and secondary amines at a temperature in the range from 60 to 300° C. in the presence of a copper-containing catalyst, wherein the catalytically active composition of the catalyst prior to reduction with hydrogen comprises from 20 to 85% by weight of aluminum oxide ($Al_2O_3$), zirconium dioxide ($ZrO_2$), titanium dioxide ($TiO_2$) and/or silicon dioxide ($SiO_2$), from 1 to 70% by weight of oxygen-containing compounds of copper, calculated as CuO, from 0 to 50% by weight of oxygen-containing compounds of magnesium, calculated as MgO, oxygen-containing compounds of chromium, calculated as $Cr_2O_3$, oxygen-containing compounds of zinc, calculated as ZnO, oxygen-containing compounds of barium, calculated as BaO, and/or oxygen-containing compounds of calcium, calculated as CaO, and less than 30% by weight of oxygen-containing compounds of nickel, calculated as NiO, based on the oxygen-containing compounds of copper, calculated as CuO, and the reaction is carried out isothermally in the gas phase in a tube reactor.

23 Claims, No Drawings

METHOD FOR THE CONTINUOUS PRODUCTION OF AN AMINE

CROSS REFERENCE TO RELATED APPLICATIONS

This application is a National Phase of PCT/EP2005/004817, filed May 4, 2005, which claims priority to German Application No. 10 2004 023 529.5, filed May 13, 2004. The entire contents of each of the above-applications are incorporated herein by reference.

The present invention relates to a process for the continuous preparation of an amine by reaction of a primary or secondary alcohol, aldehyde and/or ketone with hydrogen and a nitrogen compound selected from the group consisting of ammonia, primary and secondary amines at a temperature in the range from 80 to 300° C. in the presence of a copper-containing catalyst.

The process products are used, inter alia, as intermediates in the production of fuel additives (U.S. Pat. No. 3,275,554; DE-A-21 25 039 and DE-A-36 11 230), surfactants, drugs and crop protection agents, hardeners for epoxy resins, catalysts for polyurethanes, intermediates for the preparation of quaternary ammonium compounds, plasticizers, corrosion inhibitors, synthetic resins, ion exchangers, textile assistants, dyes, vulcanization accelerators and/or emulsifiers.

EP-A-257 443 (BASF AG) relates to a process for the preparation of trialkylamines (e.g. dimethylethylamine) by reaction of ammonia with alcohols in the presence of an alkali metal hydroxide in the liquid phase over a catalyst consisting essentially of only copper.

EP-A-542 039 (BASF AG) describes a process for the preparation of cyclic amines, e.g. N,N-dimethylcyclohexylamine, by reductive amination of ketones in the gas phase over zeolites in a shell-and-tube reactor under isothermal conditions.

EP-A-227 904 (BASF AG) teaches the preparation of dimethylethylamine or N,N-dimethylcyclohexylamine in the liquid phase by reaction of dimethylamine with cyclohexanol in the presence of an alkali metal hydroxide and a catalyst which contains essentially only copper as active metal or is a pure copper catalyst.

U.S. Pat. No. 4,910,304 (BASF AG) discloses the preparation of N-methylpiperidine and N-methylmorpholine by reaction of pentanediol or diethylene glycol (DEG) with methylamine and 45% strength aqueous KOH solution over an all-active Cu/Al catalyst at 245° C. and 250 bar.

EP-A-137 478 (BASF AG) relates to processes for the preparation of N-methylpiperidine or N-methylmorpholine by catalytic amination of pentanediol with methylamine in the gas phase at from 5 to 25 bar over a copper-containing catalyst which has been obtained by heating of a basic copper- and aluminum-containing carbonate. carbonate.

EP-A-816 350 (BASF AG) describes a process for the preparation of N-methylpiperidine and N-methylmorpholine by reaction of a primary amine with a diol in the liquid or gas phase over a copper catalyst which has been obtained by impregnation of $SiO_2$ spheres with a basic copper carbonate.

U.S. Pat. No. 4,739,051 (BASF AG) teaches the preparation of morpholine and piperidine in yields of 97 and 95%, respectively, by reaction of DEG or pentanediol with ammonia under hydrogenation conditions in the gas phase at atmospheric pressure and 200° C. over an all-active Cu/Ni/Al catalyst.

EP-A-167 872 (BASF AG) describes the preparation of N,N-dimethylalkanols or N,N,N',N'-tetramethylalkylenediamines over a copper-containing catalyst which has been obtained by heating a basic copper- and aluminum-containing carbonate.

DE-A-19 85 9776 (BASF AG) relates to the preparation of amines (e.g. dimethylethylamine, bis(2-dimethylaminoethyl) ether (Niax) and isopropylamine by reaction of alcohols or aldehydes or ketones with amines over a catalyst which comprises copper and $TiO_2$ and to which metallic copper has been added prior to shaping of the catalyst material.

JP-A-02 111 765 (Kawaken Finechemical) describes the reaction of 2,6-dimethyl-morpholine or 3,5-dimethylmorpholine or 3,6-dimethylmorpholine with diethylene glycol in the liquid phase in an autoclave. The reactions are carried out batchwise over a Raney cobalt catalyst. A disadvantage is the long reaction times of from 15 to 76 h required to obtain good yields. Although an increase in the temperature leads to shorter times, it also leads to poorer yields.

HU-A-212713 claims the synthesis of bis(morpholinoethyl) ether from morpholine and DEG in the liquid phase over a heterogeneous catalyst. In continuous operation at 50 bar, yields of up to ≧80% were obtained at space velocities of 0.02-0.1 $h^{-1}$ over a Cu,Cr catalyst. About 13% of by-products which could not be used further after being separated off were typically formed.

DE-A-100 53 386 (Air Products) describes the elimination of water from N,N-dimethylaminoethanol in the gas phase over basic zeolites to form bis(N,N-dimethyl-aminoethyl) ether. At a partial conversion, considerable amounts of three coproducts, namely N,N'-dimethylpiperazine, N-methylmorpholine and N,N,N',N'-tetramethyl-1,3-ethanediamine, are formed, and these cannot be recycled.

EP-A2-514 692 (BASF AG) discloses processes for the preparation of amines from alcohols in the presence of catalysts comprising copper and nickel and zirconium oxide and/or aluminum oxide.

EP-A-1 020 455 (BASF AG) relates to a process for the preparation of bis(2-morpholinoethyl) ether by reaction of diethylene glycol (DEG) with ammonia under superatmospheric pressure and at elevated temperature in the presence of hydrogen and a copper-containing hydrogenation catalyst.

It is an object of the present invention to find an improved economical process for the preparation of an amine. In particular, the process should make it possible to achieve better yields, space-time yields (STYs) and selectivities and be associated with increased safety with regard to possible runaway reactions.

[Space-time yields are reported in "Amount of product/(catalyst volume·time)" (kg/($l_{cat}$·h)) and/or "Amount of product/(reactor volume·time)" (kg/($l_{reactor}$·h))].

We have accordingly found a process for the continuous preparation of an amine by reaction of a primary or secondary alcohol, aldehyde and/or ketone with hydrogen and a nitrogen compound selected from the group consisting of ammonia, primary and secondary amines at a temperature in the range from 60 to 300° C. in the presence of a copper-containing catalyst, wherein the catalytically active composition of the catalyst prior to reduction with hydrogen comprises from 20 to 85% by weight of aluminum oxide ($Al_2O_3$), zirconium dioxide ($ZrO_2$), titanium dioxide ($TiO_2$) and/or silicon dioxide ($SiO_2$), from 1 to 70% by weight of oxygen-containing compounds of copper, calculated as CuO, from 0 to 50% by weight of oxygen-containing compounds of magnesium, calculated as MgO, oxygen-containing compounds of chromium, calculated as $Cr_2O_3$, oxygen-containing compounds of zinc, calculated as ZnO, oxygen-containing compounds of barium, calculated as BaO, and/or oxygen-containing compounds of calcium, calculated as CaO, and less than 30% by weight of oxygen-containing compounds of nickel, calculated as NiO, based on the oxygen-containing compounds of copper, calculated as CuO, and the reaction is carried out isothermally in the gas phase in a tube reactor.

The invention has accordingly recognized, inter alia, the advantageous combination of the specific catalyst with an isothermal mode of operation (amination of the starting material(s) specified) in the gas phase.

The reaction in the tube reactor in the process of the invention is very particularly preferably carried out in the gas recycle mode.

The circulating gas which preferably comprises predominantly hydrogen, serves firstly to vaporize the starting materials and secondly as reactant in the amination reaction.

In the gas recycle mode, the starting materials (alcohol, aldehyde and/or ketone, hydrogen and the nitrogen compound) are vaporized in a circulating gas stream and are fed in gaseous form into the reactor.

The starting materials (alcohol, aldehyde and/or ketone, the nitrogen compound) can also be vaporized as liquid solutions and supplied to the catalyst bed with the circulating gas stream.

Examples of suitable reactors with a circulating gas stream may be found in Ullmann's Encyclopedia of Industrial Chemistry, 5th Ed., Vol. B 4, pages 199-238, "Fixed-Bed Reactors". The reaction is very particularly preferably carried out in a shell-and-tube reactor or in a single-stream plant.

In a single-stream plant, the tube reactor in which the isothermal reaction is carried out consists of a plurality of (e.g. two or three) individual tube reactors connected in series.

The amount of circulating gas is preferably in the range from 40 to 1500 $m^3$ (at operating pressure)/[$m^3$ of catalyst (bed volume)·h], in particular in the range from 100 to 700 $m^3$ (at operating pressure)/[$m^3$ of catalyst (bed volume)·h].

The circulating gas preferably contains at least 10% by volume, in particular from 50 to 100% by volume, very particularly preferably from 80 to 100% by volume, of hydrogen.

The isothermal reaction of the process of the invention is preferably carried out with a temperature fluctuation of not more than +/−8° C., especially not more than +/−5° C., in particular not more than +/−4° C., very particularly preferably not more than +/−3° C., e.g. not more than +/−0 to 2° C. or not more than +/−0 to 1° C.

These temperature fluctuations are based on the prevailing temperatures in the respective catalyst bed at the point where the starting materials enter the catalyst bed and at the point where the reaction mixtures leaves the catalyst bed. It is possible for a plurality of catalyst beds to be connected in parallel or in series.

If a plurality of catalyst beds are connected in series, the specified temperature fluctuations in the isothermal mode of operation according to the invention apply to the respective temperature in the catalyst bed at the point where the starting materials enter the first catalyst bed and where the reaction mixture leaves the last catalyst bed.

In a preferred embodiment, the temperature of the tube reactor is controlled externally by means of a stream of heat transfer medium which can be, for example, an oil, a salt melt or another liquid capable of transferring heat.

Compared to a synthesis in the liquid phase and compared to a nonisothermal synthesis in the gas phase, the reaction conditions according to the present invention have the advantage of, inter alia, better yields and greater safety in respect of runaway reactions, in particular at high reaction temperatures (e.g. from 200 to 300° C.). The isothermal gas-phase mode of operation greatly reduces the potential for a runaway reaction during the synthesis. The mass of material present in the reactor which would be available for a runaway reaction is only a fraction of the mass present in a liquid-phase process.

In the process of the invention, the catalysts are preferably used in the form of catalysts which consist entirely of catalytically active composition and optionally a shaping aid (e.g. graphite or stearic acid) if the catalyst is to be used as shaped bodies, i.e. contain no further catalytically active accompanying substances.

In this context, the oxidic support materials titanium dioxide ($TiO_2$), aluminum oxide ($Al_2O_3$), zirconium dioxide ($ZrO_2$) and silicon dioxide ($SiO_2$) are considered to be part of the catalytically active composition.

To use the catalysts, the catalytically active composition to be milled to powder is introduced into the reaction vessel or the catalytically active composition is installed in the reactor as shaped catalyst bodies after milling, mixing with shaping aids, shaping and heat treatment, for example as pellets, spheres, rings, extrudates (e.g. extruded rods).

The figures (in % by weight) given for the concentrations of the components of the catalyst are, unless indicated otherwise, in each case based on the catalytically active composition of the finished catalyst after its last heat treatment and before it has been reduced by means of hydrogen.

The catalytically active composition of the catalyst after its last heat treatment and before it has been reduced by means of hydrogen is defined as the sum of the catalytically active constituents and the abovementioned catalyst support materials and consists essentially of the following constituents:

Titanium dioxide ($TiO_2$) and/or aluminum oxide ($Al_2O_3$) and/or zirconium dioxide ($ZrO_2$) and/or silicon dioxide ($SiO_2$) and oxygen-containing compounds of copper and optionally oxygen-containing compounds of magnesium and/or of chromium and/or of zinc and/or of barium and/or of calcium and optionally oxygen-containing compounds of nickel, with the amount of these oxygen-containing compounds of nickel, calculated as NiO, based on the amount of oxygen-containing compounds of copper, calculated as CuO, is less than 20% by weight.

The sum of the abovementioned constituents of the catalytically active composition, calculated as $Al_2O_3$, $ZrO_2$, $TiO_2$, $SiO_2$, CuO, MgO, $Cr_2O_3$, ZnO, BaO, CaO and NiO, is usually from 70 to 100% by weight, preferably from 80 to 100% by weight, particularly preferably from 90 to 100% by weight, very particularly preferably 100% by weight.

The catalytically active composition of the catalysts used in the process of the invention can further comprise one or more elements (oxidation state 0) or their inorganic or organic compounds selected from groups I A to VI A and I B to VII B and VII of the Periodic Table.

Examples of such elements and their compounds are:

transition metals such as Co and CoO, Re and rhenium oxides, Mn and $MnO_2$, Mo and molybdenum oxides, W and tungsten oxides, Ta and tantalum oxides, Nb and niobium oxides or niobium oxalate, V and vanadium oxides and vanadyl pyrophosphate;

lanthanides such as Ce and $CeO_2$ or Pr and $Pr_2O_3$; alkali metal oxides such as $Na_2O$;

alkali metal carbonates; alkaline earth metal oxides such as SrO; alkaline earth metal carbonates such as $MgCO_3$, $CaCO_3$ and $BaCO_3$; boron oxide ($B_2O_3$).

The catalytically active composition of the catalysts used in the process of the invention comprises, after its last heat treatment and before it has been reduced by means of hydrogen, from 20 to 85% by weight, preferably from 25 to 80% by weight, particularly preferably from 30 to 75% by weight, of aluminum oxide ($Al_2O_3$) and/or zirconium dioxide ($ZrO_2$) and/or titanium dioxide ($TiO_2$) and/or silicon dioxide ($SiO_2$) and from 1 to 70% by weight, preferably from 2 to 65% by weight, particularly preferably from 5 to 60% by weight, very particularly preferably from 20 to 60% by weight, of oxygen-containing compounds of copper, calculated as CuO, from 0 to 50% by weight, preferably from 0 to 30% by weight, particularly preferably from 0 to 20% by weight, of oxygen-containing compounds of magnesium, calculated as MgO, and/or oxygen-containing compounds of chromium, calculated as $Cr_2O_3$, and/or oxygen-containing compounds of zinc, calculated as ZnO, and/or oxygen-containing compounds of barium, calculated as BaO, and/or oxygen-containing compounds of calcium, calculated as CaO, and less than 30% by weight, e.g. 5-28% by weight, preferably less than 25% by weight, e.g. less than 20% by weight, in particular less than 10% by weight, for example less than 5% by weight or 0-1% by weight, of oxygen-containing compounds of nickel, calculated as NiO, based on the oxygen-containing compounds of copper, calculated as CuO.

The catalytic composition of preferred catalysts comprises from 20 to 85% by weight, preferably from 25 to 80% by weight, particularly preferably from 30 to 75% by weight, of aluminum oxide ($Al_2O_3$) and/or silicon dioxide ($SiO_2$) and no oxygen-containing compounds of zirconium and titanium.

The oxygen-containing compounds of copper are, in particular, copper(I) oxide and copper(II) oxide, preferably copper(II) oxide.

The catalysts used in the process of the invention can be prepared by various methods. They can be obtained, for example, by peptizing pulverulent mixtures of hydroxides, carbonates, oxides and/or other salts of the components aluminum, zirconium, titanium, silicon, copper, magnesium, chromium, zinc, barium and calcium with water and subsequently extruding and heat treating the mass obtained in this way.

The catalysts in the process of the invention can also be produced by impregnating zirconium dioxide ($ZrO_2$), titanium dioxide ($TiO_2$), aluminum oxide ($Al_2O_3$), silicon dioxide ($SiO_2$) or mixtures of two or more of these inorganic oxides which are, for example, in the form of powder or shaped bodies such as extrudates, pellets, spheres or rings.

Aluminum oxide can be used in various modifications, with preference being given to α-, γ- (gamma) or θ-$Al_2O_3$.

Zirconium dioxide is used, for example, in the monoclinic or tetragonal form, preferably in the monoclinic form, and titanium dioxide is preferably used as anatase or rutile.

Silicon dioxide suitable as support material can be obtained, for example, via precipitation from water glass or via the sol-gel process or be used as mesoporous $SiO_2$ or silica gel (e.g. as described in *Ullmann, Enzykl. Techn. Chem.*, 4th edition, Volume 21, pp. 457-63, 1982) or in the form of silicates such as bentonite, montmorillonite, kaolin, hectorite or aluminosilicates (e.g. as described in Nature Volume 359, pp. 710-12, 1992, or alkali metal or alkaline earth metal aluminosilicates (zeolites), e.g. of the general formula $M_{2/z}O \cdot Al_2O_3 \cdot x\,SiO_2 \cdot y\,H_2O$, where M is a monovalent or polyvalent metal, H, $[NH_4]$, z is the valence, x=1.8 to about 12 and y=0 to about 8), magnesium silicates (e.g. steatite), zirconium silicates, cerium silicates or calcium silicates.

The shaped bodies of the abovementioned inorganic oxides can be produced by the customary methods.

The impregnation of these inorganic oxides is likewise carried out by customary methods, as described, for example, in EP-A-599 180, EP-A-673 918 or A. B. Stiles, Catalyst Manufacture—Laboratory and Commercial Preparations, Marcel Dekker, New York (1983), by application of an appropriate metal salt solution in one or more impregnation stages using, for example, appropriate nitrates, acetates or chlorides as metal salts. After impregnation, the composition is dried and, if appropriate, calcined.

Impregnation can also be carried out by the “incipient wetness” method in which the inorganic oxide or the mixture of inorganic oxides is moistened at most to saturation with the impregnation solution, in accordance with its water absorption capacity. However, impregnation can also be carried out in an excess of solution.

In the case of multistage impregnation processes, it is advantageous to dry and if appropriate calcine the material to be impregnated between individual impregnation steps. Multistage impregnation is particularly advantageous when the inorganic oxide or the mixture of inorganic oxides is to be loaded with a relatively large amount of metal.

To apply a plurality of metal components to the inorganic oxide or the mixture of inorganic oxides, impregnation can be carried out using all metal salts simultaneously or using the individual metal salts successively in any order.

However, preference is given to employing precipitation methods for producing catalysts used in the process of the invention. They can, for example, be obtained by coprecipitation of the copper, magnesium, chromium, zinc, barium and calcium components from an aqueous salt solution in which these elements are present by means of mineral bases in the presence of a slurry of a sparingly soluble, oxygen-containing aluminum, titanium, silicon and/or zirconium compound and subsequent washing, drying and calcination of the precipitate obtained. As sparingly soluble, oxygen-containing aluminum, titanium, silicon and/or zirconium compounds, it is possible to use, for example, aluminum oxide, titanium dioxide, silicon dioxide, zirconium dioxide and zirconium oxide hydrate. The slurries of the sparingly soluble aluminum, titanium, silicon, and/or zirconium compounds can be prepared by suspending finely divided powders of these compounds in water with vigorous stirring. The slurries are advantageously obtained by precipitation of the sparingly soluble aluminum, titanium, silicon and/or zirconium compounds from aqueous aluminum, titanium, silicon and/or zirconium salt solutions by means of mineral bases.

The catalysts used in the process of the invention are preferably prepared by coprecipitation of all their components. For this purpose, it is advantageous to admix an aqueous solution in which the catalyst components are present with an aqueous mineral base, in particular an alkali metal base, for example sodium carbonate, sodium hydroxide, potassium carbonate or potassium hydroxide, while heating and stirring until precipitation is complete. The type of salts used is generally not critical: since the water solubility of the salts is of primary importance in this procedure, a criterion is for them to have the good solubility in water required for preparation of these relatively highly concentrated salt solutions. It is self-evident that when choosing the salts of the individual components, only salts having anions which do not lead to interference, either by causing undesirable precipitates or impairing or preventing precipitation as a result of complex formation, will naturally be selected.

The precipitates obtained in this precipitation reactions are generally chemically non-uniform and comprise, inter alia, mixtures of the oxides, oxide hydrates, hydroxides, carbonates and insoluble and basic salts of the metals used. To improve the filterability of the precipitates, it can be found to be useful for them to be aged, i.e. for them to be left to stand for some time after precipitation, if appropriate at elevated temperature or with air being passed through the suspension.

The precipitates obtained by these precipitation processes are processed further in a customary fashion to give the catalysts according to the invention. After washing, they are preferably dried at from 80 to 200° C., more preferably from 100 to 150° C., and then calcined. Calcination is preferably carried out at temperatures in the range from 300 to 800° C., preferably from 400 to 600° C., in particular from 450 to 550° C.

After calcination, the catalyst is advantageously conditioned, either by milling it to a particular particle size or by mixing it after milling with shaping aids such as graphite or stearic acid and pressing it by means of a pressure to form shaped bodies, e.g. pellets, and heat treating it. The heat treatment temperatures preferably correspond to the temperatures in the calcination.

In the catalysts produced in this way, the catalytically active metals are present in the form of a mixture of their oxygen-containing compounds, i.e. especially as oxides and mixed oxides.

The catalysts produced in this way are stored as such and, if appropriate, sold. Before used as catalysts, they are usually prereduced. However, they can also be used without prereduction, in which case they are then reduced by the hydrogen present in the reactor under the conditions of the hydrogenative amination.

To carry out the prereduction, the catalysts are firstly exposed to a nitrogen/hydrogen atmosphere at preferably from 150 to 200° C. for a period of, for example, from 12 to 20 hours and subsequently treated in a hydrogen atmosphere at preferably from 200 to 400° C. for up to about 24 hours. In this prereduction, part of the oxygen-containing metal compounds present in the catalysts is reduced to the corresponding metals, so that the latter are present together with the various oxygen compounds in the active form of the catalyst.

The catalysts of the general formula $M_xMg_y(SiO_2).n\ H_2O$, where M is a divalent, reducible metal atom from the group consisting of Cu, Fe, Co and Ni, x and y are numbers which together can reach a value of 1.5 and n is, expressed in % by weight after drying, from 0 to 80, disclosed in EP-A-284 919, for example the catalyst which is described in the example in loc. cit. and comprises 35% of CuO, 9% of MgO and 38% of $SiO_2$ and the catalyst described on page 3 of EP-A-863 140 and comprises from 45 to 47% by weight of CuO, magnesium silicate comprising from about 15 to 17% by weight of MgO and from 35 to 36% by weight of $SiO_2$, about 0.9% by weight of $Cr_2O_3$, about 1% by weight of BaO and about 0.6% by weight of ZnO, and the supported catalysts which are disclosed in WO 95/32171 and EP-A-816 350 and comprise from 5 to 50% by weight, preferably from 15 to 40% by weight, of copper, calculated as CuO, from 50 to 95% by weight, preferably from 60 to 85% by weight, of silicon, calculated as $SiO_2$, from 0 to 20% by weight of magnesium, calculated as MgO, from 0 to 5% by weight of barium, calculated as BaO, from 0 to 5% by weight of zinc, calculated as ZnO, and from 0 to 5% by weight of chromium, calculated as $Cr_2O_3$, in each case based on the total weight of the calcined catalyst, for example the catalyst which is disclosed in EP-A-816 350, page 5, and comprises 30% by weight of CuO and 70% by weight of $SiO_2$, are preferably used in the process of the invention.

The process of the invention is particularly preferably carried out using the catalysts disclosed in DE-A-24 45 303, which are obtainable by heat treatment of a basic copper- and aluminum-containing carbonate of the general composition $Cu_mAl_6(CO_3)_{0.5m}O_3(OH)_{m+12}$, where m is any, not necessarily integral, value of from 2 to 6, at a temperature of from 350 to 700° C., for example the copper-containing precipitated catalyst which is disclosed in loc. cit., Example 1, and is prepared by treating a solution of copper nitrate and aluminum nitrate with sodium bicarbonate and subsequently washing, drying and heat treating the precipitate, the catalysts disclosed in EP-A-514 692, whose catalytically active composition prior to reduction with hydrogen comprises from 5 to 100% by weight of an oxide of copper and nickel in an atomic ratio of from 1:1 to 10:1 and zirconium oxide and/or aluminum oxide, in particular the catalysts which are disclosed in loc. cit. on page 3, lines 20 to 30, and whose catalytically active composition prior to reduction with hydrogen comprises from 20 to 80% by weight, in particular from 40 to 70% by weight, of $Al_2O_3$ and/or $ZrO_2$, from 1 to 30% by weight of CuO, from 1 to 30% by weight of NiO and, if appropriate, from 1 to 30% by weight of CoO, for example the catalyst which is described in loc. cit., Example 1, and comprises (after activation) 55% by weight of $Al_2O_3$, 36% by weight of Cu and 7% by weight of Ni.

The process of the invention is carried out continuously, with the catalyst preferably being installed as a fixed bed in the reactor. Flow into the fixed catalyst bed can occur either from above or from below. The temperature, pressure and amount of the gas stream are set so that even relatively high-boiling reaction products remain in the gas phase.

The amine component (nitrogen compound) is preferably used in a molar amount corresponding to from 0.90 to 100 times, in particular from 1.0 to 10 times, the molar amount of the alcohol, aldehyde and/or ketone used.

The process of the invention is preferably carried out at an absolute pressure in the range from 1 to 300 bar, preferably from 1 to 50 bar, particularly preferably from 1 to 30 bar.

In the case of an amination of an alcohol, the process of the invention is preferably carried out at a temperature in the range from 80 to 300° C., preferably from 150 to 250° C., particularly preferably from 170 to 230° C.

In the case of an amination of an aldehyde and/or ketone, the process of the invention is preferably carried out at a temperature in the range from 60 to 200° C., preferably from 80 to 170° C., particularly preferably from 100 to 150° C.

The process is preferably operated with an amount of off-gas of from 5 to 800 standard cubic meters/h, in particular from 20 to 300 standard cubic meters/h.

The space velocity over the catalyst is preferably in the range from 0.1 to 2.0 kg, preferably from 0.1 to 1,0 kg, particularly preferably from 0.2 to 0.6 kg, of alcohol, aldehyde and/or ketone per liter of catalyst (bed volume) and hour.

It is possible to employ higher temperatures, higher total pressures and higher space velocities over the catalyst. The pressure in the reactor, which is the sum of the partial pressures of the aminating agent, the alcohol, aldehyde and/or ketone component and the reaction products formed at the indicated temperatures, is advantageously increased to the desired reaction pressure by injection of hydrogen.

The water of reaction formed during the course of the reaction generally does not have any adverse effect on the conversion, the reaction rate, the selectivity and the operating life of the catalyst and is therefore advantageously removed from the reaction product only during work-up of the latter, e.g. by distillation.

After the output from the reactor has advantageously been depressurized, the excess hydrogen and any excess aminating agent present are removed and the crude reaction product obtained is purified, e.g. by fractional rectification. Suitable work-up methods are described, for example, in EP-A-1 312 600 and EP-A-1 312 599 (both BASF AG).

Unreacted starting materials and any suitable by-products formed can be recirculated to the synthesis. Unreacted starting materials can, after condensation of the products in a separator, be passed again over the catalyst bed in the circulating gas stream, either continuously or batchwise.

Apart from ammonia, suitable aminating agents for use in the process of the invention are primary and secondary amines which can, as a result of their boiling points, be kept in the gas phase within the process parameter range in the process. The same applies to the process product amines and the process feedstocks (alcohol, aldehyde, ketone).

The process of the invention can be used to prepare, for example, amines of the formula I (I)

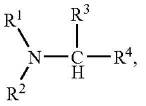

where $R^1$, $R^2$ are each hydrogen (H), alkyl such as $C_{1-20}$-alkyl, cycloalkyl such as $C_{3-12}$-cycloalkyl, alkoxyalkyl such as $C_{2-30}$-alkoxyalkyl, dialkylaminoalkyl such as $C_{3-30}$-dialkylaminoalkyl, aryl, aralkyl such as $C_{7-20}$-aralkyl and alkylaryl such as $C_{7-20}$-alkylaryl, or together form $—(CH_2)—X—(CH_2)_k—$, $R^3$ $R^4$ are each hydrogen (H), alkyl such as $C_{1-20}$-alkyl, cycloalkyl such as $C_{3-12}$-cycloalkyl, hydroxyalkyl such as $C_{1-20}$-hydroxyalkyl, aminoalkyl such as $C_{1-20}$-aminoalkyl, hydroxyalkylaminoalkyl such as $C_{2-20}$-hydroxyalkylaminoalkyl, alkoxyalkyl such as $C_{2-30}$-alkoxyalkyl, dialkylaminoalkyl such as $C_{3-30}$-dialkylaminoalkyl, alkylaminoalkyl such as $C_{2-30}$-alkylaminoalkyl, $R_5$—$(OCR^6R^7CR^8R^9)_n$ —$(OCR^6R^7)$, aryl, heteroaryl, aralkyl such as $C_{7-20}$-aralkyl, heteroarylalkyl such as $C_{4-20}$-heteroarylalkyl, alkylaryl such as $C_{7-20}$-alkylaryl, alkylheteroaryl such as $C_{4-20}$-alkylheteroaryl and $Y—(CH_2)_m—NR^5—(CH_2)_q$ or together form $—(CH_2)_l—X—(CH_2)_m—$ or $R^2$ and $R^4$ together form $—(CH_2)_l—X—(CH_2)_m—$, $R^5$, $R^{10}$ are each hydrogen (H), alkyl such as $C_{1-4}$-alkyl, alkylphenyl such as $C_{7-40}$-alkylphenyl, $R^6$, $R^7$, $R^8$, $R^9$ are each hydrogen (H), methyl or ethyl, x is $CH_2$, $CHR^5$, oxygen (O), sulfur (S) or $NR^5$, Y is $N(R^{10})_2$, hydroxy, $C_{2-20}$-alkylaminoalkyl or $C_{3-20}$-dialkylaminoalkyl, n is an integer from 1 to 30 and j, k, l, m, q are each an integer from 1 to 4.

The process of the invention is therefore preferably employed for preparing an amine I by reacting a primary or secondary alcohol of the formula II (II)

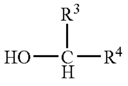

and/or aldehyde and/or ketone of the formula VI or VII (VI)

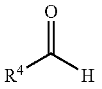

(VII)

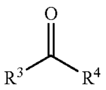

with a nitrogen compound of the formula III (III)

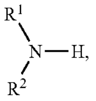

where $R^1$, $R^2$, $R^3$ and $R^4$ are as defined above.

The starting alcohol can also be an amino alcohol, e.g. an amino alcohol of the formula II.

As the definitions of the radicals $R^2$ and $R^4$ indicate, the reaction can also occur intramolecularly in an appropriate amino alcohol, amino ketone or amino aldehyde.

Accordingly, to prepare the amine I, a hydrogen atom of the nitrogen compound III is replaced purely formally by the radical $R^4(R^3)CH$—with liberation of one molar equivalent of water.

Preference is also given to employing the process of the invention in the preparation of a cyclic amine of the formula IV (IV)

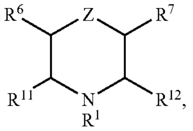

where $R^{11}$ and $R^{12}$ are each hydrogen (H), alkyl such as $C_1$-$C_{20}$-alkyl, cycloalkyl such as $C_3$-$C_{12}$-cycloalkyl, aryl, heteroaryl, aralkyl such as $C_7$-$C_{20}$-aralkyl and alkylaryl such as $C_7$-$C_{20}$-alkylaryl, Z is $CH_2$, $CHR^5$, oxygen (O), $NR^5$ or $NCH_2CH_2OH$ and $R^1$, $R^6$, $R^7$ are as defined above, by reaction of an alcohol of the formula V (V)

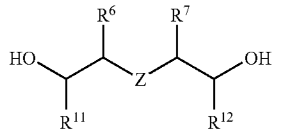

with ammonia or a primary amine of the formula VI $R^1—NH_2$ (VI).

The substituents $R^1$ to $R^{12}$, the variables X, Y, Z and the indices j, k, l, m, n and q in the compounds I, II, III, IV, V, VI and VII have, independently of one another, the following meanings:

$R^1$, $R^2$, $R^3$, $R^4$, $R^5$, $R^6$, $R^7$, $R^8$, $R^9$, $R^{10}$, $R^{11}$, $R^{12}$:

hydrogen (H), $R^3$, $R^4$:

alkyl such as $C_{1-20}$-alkyl, preferably $C_{1-14}$-alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl, hydroxyalkyl such as $C_{1-20}$-hydroxyalkyl, preferably $C_{1-8}$-hydroxyalkyl, particularly preferably $C_{1-4}$-hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-(hydroxymethyl)ethyl, aminoalkyl such as $C_{1-20}$-aminoalkyl, preferably $C_{1-8}$-aminoalkyl such as aminoethyl, 2-aminoethyl, 2-amino-,1-dimethylethyl, 2-amino-n-propyl, 3-amino-n-propyl, 4-amino-n-butyl, 5-amino-n-pentyl, N-(2-aminoethyl)-2-aminoethyl and N-(2-aminoethyl)aminoethyl, hydroxyalkylaminoalkyl such as $C_{2-20}$-hydroxyalkylaminoalkyl, preferably $C_{3-8}$-hydroxyalkylaminoalkyl such as (2-hydroxyethylamino)methyl, 2-(2-hydroxyethylamino)ethyl and 3-(2-hydroxyethylamino)propyl, $R^5—(OCR^6R^7CR^8R^9)_n—(OCR^6R^7)$ preferably $R^5—(OCHR^7CHR^9)_n—(OCR^6R^7)$, particularly preferably $R^5—(OCH_2CHR^9)_n—(OCR^6R^7)$, alkylaminoalkyl such as $C_{2-30}$-alkylaminoalkyl, preferably $C_{2-20}$-alkylaminoalkyl, particularly preferably $C_{2-8}$-alkylaminoalkyl such as methylaminomethyl, 2-methylaminoethyl, ethylaminomethyl, 2-ethylaminoethyl and 2-(isopropylamino)ethyl, $(R^5)HN—(CH_2)_q$, $Y—(CH_2)_m—NR^5—(CH_2)_q$, heteroarylalkyl such as $C_{4-20}$-heteroarylalkyl, e.g. pyrid-2-ylmethyl, furan-2-yl-methyl, pyrrol-3-ylmethyl and imidazol-2-ylmethyl, alkylheteroaryl such as $C_{4-20}$-alkylheteroaryl. e.g. 2-methyl-3-pyridinyl, 4,5-dimethylimidazol-2-yl, 3-methyl-2-furanyl and 5-methyl-2-pyrazinyl, heteroaryl such as 2-pyridinyl, 3-pyridinyl, 4-pyridinyl, pyrazinyl, pyrrol-3-yl, imidazol-2-yl, 2-furanyl and 3-furanyl, $R^1$, $R^2$, $R^3$, $R^4$:

cycloalkyl such as $C_{3-12}$-cycloalkyl, preferably $C_{3-8}$-cycloalkyl such as cyclopropyl, cyclobutyl, cyclopentyl, cyclohexyl, cycloheptyl and cyclooctyl, particularly preferably cyclopentyl and cyclohexyl, alkoxyalkyl such as $C_{2-30}$-alkoxyalkyl, preferably $C_{2-20}$-alkoxyalkyl, particularly preferably $C_{2-8}$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_{2-4}$-alkoxyalkyl, dialkylaminoalkyl such as $C_{3-30}$-dialkylaminoalkyl, preferably $C_{3-20}$-dialkylaminoalkyl, particularly preferably $C_{3-10}$-dialkylaminoalkyl such as N,N-dimethylaminomethyl, (N,N-dibutylamino)methyl, 2-(N,N-dimethylamino)ethyl, 2-(N,N-diethylamino)ethyl, 2-(N,N-dibutylamino)ethyl, 2-(N,N-di-n-propylamino)ethyl and 2-(N,N-diisopropylamino)ethyl, 3-(N,N-dimethylamino)propyl, $(R^5)_2N—(CH_2)_q$, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, alkylaryl such as $C_{7-20}$-alkylaryl, preferably $C_{7-12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, aralkyl such as $C_{7-20}$-aralkyl, preferably $C_{7-12}$-phenylalkyl such as benzyl, p-methoxybenzyl, 3,4-dimethoxybenzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, $R^3$ and $R^4$ or $R^2$ and $R^4$ together a $—(CH_2)_l—X—(CH_2)_m—$ group such as $—(CH_2)_3—$, $—(CH_2)_4—$, $—(CH_2)_5—$, $—(CH_2)_6—$, $—(CH_2)_7—$, $—(CH_2)—O—(CH_2)_2—$, $—(CH_2)—NR^5—(CH_2)_2—$, $—(CH_2)—CHR^5—(CH_2)_2—$, $—(CH_2)_2—O—(CH_2)_2—$, $—(CH_2)_2—NR^5—(CH_2)_2—$, $—(CH_2)_2—CHR^5—(CH_2)_2—$, $—CH_2—O—(CH_2)_3—$, $—CH_2—NR^5—(CH_2)_3—$, $—CH_2—CHR^5—(CH_2)_3—$, $R^1$, $R^2$:

alkyl such as $C_{1-20}$-alkyl, preferably $C_{1-8}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, particularly preferably $C_{1-4}$-alkyl, or $R^1$ and $R^2$ together a $—(CH_2)_j—X—(CH_2)_k—$ group such as $—(CH_2)_3—$, $—(CH_2)_4—$, $—(CH_2)_5—$, $—(CH_2)_6—$, $—(CH_2)_7—$, $—(CH_2)—O—(CH_2)_2—$, $—(CH_2)—NR^5—(CH_2)_2—$, $—(CH_2)—CHR^5—(CH_2)_2—$, $—(CH_2)_2—O—(CH_2)_2—$, $—(CH_2)_2—NR^5—(CH_2)_2—$, $—(CH_2)_2—CHR^5—(CH_2)_2—$, $—CH_2—O—(CH_2)_3—$, $—CH_2—NR^5—(CH_2)_3—$, $—CH_2—CHR^5—(CH_2)_3—$, $R^5$, $R^{10}$:

alkyl, preferably $C_{1-4}$-alkyl such as methyl, ethyl, n-propyl, isopropyl, n-butyl, iso-butyl, sec-butyl and tert-butyl, preferably methyl and ethyl, particularly preferably methyl, alkylphenyl, preferably $C_{7-40}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, in particular $C_{7-20}$-alkylphenyl, $R^6$, $R^7$, $R^8$, $R^9$:

methyl or ethyl, preferably methyl, $R^{11}$, $R^{12}$:

alkyl such as $C_1$-$C_{20}$-alkyl, cycloalkyl such as $C_3$-$C_{12}$-cycloalkyl, aryl, heteroaryl, aralkyl such as $C_7$-$C_{20}$-aralkyl and alkylaryl such as $C_7$-$C_{20}$-alkylaryl, in each case as defined above,

X:

$CH_2$, $CHR^5$, oxygen (O), sulfur (S) or $NR^5$, preferably $CH_2$ and O,

Y:

$N(R^{10})_2$, preferably $NH_2$ and $N(CH_3)_2$, hydroxy (OH), $C_{2-20}$-alkylaminoalkyl, preferably $C_{2-16}$-alkylaminoalkyl such as methylaminomethyl, 2-methylaminoethyl, ethylaminomethyl, 2-ethylaminoethyl and 2-(isopropylamino)ethyl, $C_{3-20}$-dialkylaminoalkyl, preferably $C_{3-16}$-dialkylaminoalkyl such as dimethylaminomethyl, 2-dimethylaminoethyl, 2-diethylaminoethyl, 2-(di-n-propylamino)ethyl and 2-(diisopropylamino)ethyl,

Z:

$CH_2$, $CHR^5$, O, $NR^5$ or $NCH_2CH_2OH$, j, l:

an integer from 1 to 4 (1, 2, 3 or 4), preferably 2 and 3, particularly preferably 2, k, m, q:

an integer from 1 to 4 (1, 2, 3 or 4), preferably 2, 3 and 4, particularly preferably 2 and 3, n:

an integer from 1 to 30, preferably an integer from 1 to 8 (1, 2, 3, 4, 5, 6, 7 or 8), particularly preferably an integer from 1 to 6.

Suitable alcohols are, subject to the abovementioned conditions, virtually all primary and secondary alcohols having an aliphatic OH function. The alcohols can be linear, branched or cyclic. Secondary alcohols are aminated just like primary alcohols. The alcohols can also bear substituents or contain functional groups which are inert under the conditions of the hydrogenative amination, for example alkoxy, alkenyloxy, alkylamino or dialkylamino groups, or may be hydrogenated under the conditions of the hydrogenative amination, for example CC double or triple bonds. If polyhydric alcohols are to be aminated, it is possible to obtain amino alcohols, cyclic amines or multiply aminated products preferentially by controlling the reaction conditions.

The amination of 1,4-diols leads, depending on the choice of reaction conditions, to 1-amino-4-hydroxy compounds, 1,4-diamino compounds or five-membered rings containing a nitrogen atom (pyrrolidines).

The amination of 1,6-diols leads, depending on the choice of reaction conditions, to 1-amino-6-hydroxy compounds, 1,6-diamino compounds or seven-membered rings containing a nitrogen atom (hexamethylenimines).

The amination of 1,5-diols leads, depending on the choice of reaction conditions, to 1-amino-5-hydroxy compounds, 1,5-diamino compounds or six-membered rings containing a nitrogen atom (piperidines). Accordingly, amination of diglycol by means of $NH_3$ can give monoaminodiglycol (=ADG=$H_2N$—$CH_2CH_2$—O—$CH_2CH_2$—OH), diaminodiglycol or particularly preferably morpholine. Correspondingly, piperazine is particularly preferably obtained from diethanolamine. N-(2-hydroxyethyl)piperazine can be obtained from triethanolamine.

Preference is given to aminating, for example, the following alcohols:

methanol, ethanol, n-propanol, isopropanol, n-butanol, isobutanol, n-pentanol, n-hexanol, 2-ethylhexanol, tridecanol, stearyl alcohol, palmityl alcohol, cyclobutanol, cyclopentanol, cyclohexanol, benzyl alcohol, 2-phenylethanol, 2-(p-methoxyphenyl)-ethanol, 2-(3,4-dimethoxyphenyl)ethanol, 1-phenyl-3-butanol, ethanolamine, n-pro-panolamine isopropanolamine, 2-amino-1-propanol, 1-methoxy-2-propanol, 3-amino-2,2-dimethyl-1-propanol, n-pentanolamine (1-amino-5-pentanol), n-hexanolamine (1-amino-6-hexanol), ethanolamine, diethanolamine, triethanolamine, N-alkyldiethanolamines, diisopropanolamine, 3-(2-hydroxyethylamino)propan-1-ol, 2-(N,N-dimethylamino)ethanol, 2-(N,N-diethylamino)ethanol, 2-(N,N-di-n-propylamino)ethanol, 2-(N,N-diisopropylamino)ethanol, 2-(N,N-di-n-butylamino)ethanol, 2-(N,N-diisobutyl-amino)ethanol, 2-(N,N-di-sec-butylamino)ethanol, 2-(N,N-di-tert-butylamino)ethanol, 3-(N,N-dimethylamino)propanol, 3-(N,N-diethylamino)propanol, 3-(N,N-di-n-propyl-amino)propanol, 3-(N,N-diisopropylamino)propanol, 3-(N,N-di-n-butylamino)propanol, 3-(N,N-diisobutylamino)propanol, 3-(N,N-di-sec-butylamino)propanol, 3-(N,N-di-tert-butylamino)propanol, 1-dimethylamino4-pentanol, 1-diethylamino4-pentanol, ethylene glycol, 1,2-propylene glycol, 1,3-propylene glycol, diglycol, 1,4-butanediol, 1,5-pen-tanediol, 1,6-hexanediol, 2,2-bis[4-hydroxycyclohexyl]propane, methoxyethanol, propoxyethanol, butoxyethanol, polyisobutyl alcohols, polypropyl alcohols, polyethylene glycol ethers, polypropylene glycol ethers and polybutylene glycol ethers. In the process of the invention, the polyalkylene glycol ethers mentioned last are converted into the corresponding amines by transformation of the free hydroxyl groups.

Particularly preferred alcohols are methanol, ethanol, n-propanol, i-propanol, n-butanol, sec-butanol, 1,4-butanediol, 1,5-pentanediol, 1,6-hexanediol, 2-ethylhexanol, cyclohexanol, fatty alcohols, ethylene glycol, diethylene glycol (DEG), triethylene glycol (TEG), 2-(2-dimethylaminoethoxy)ethanol, N-methyldiethanolamine and 2-(2-di-methylaminoethoxy)ethanol.

Ketones which can be used in the process of the invention subject to the abovementioned conditions are virtually all aliphatic and aromatic ketones. The aliphatic ketones can be linear, branched or cyclic, and can contain hetero atoms. The ketones can also bear substituents or contain functional groups which are inert under the conditions of the hydrogenative amination, for example alkoxy, alkenyloxy, alkylamino or dialkylamino groups, or may also be hydrogenated under the conditions of the hydrogenative amination, for example CC double or triple bonds. If polyfunctional ketones are to be aminated, amino ketones, amino alcohols, cyclic amines or multiply aminated products can be obtained by controlling the reaction conditions.

Preference is given to aminatively hydrogenating, for example, the following ketones:

acetone, ethyl methyl ketone, methyl vinyl ketone, isobutyl methyl ketone, butanone, 3-methylbutan-2-one, diethyl ketone, tetralone, acetophenone, p-methylacetophenone, p-methoxyacetophenone, m-methoxyacetophenone, 1-acetyinaphthalene, 2-acetyl-naphthalene, 1-phenyl-3-butanone, cyclobutanone, cyclopentanone, cyclopentenone, cyclohexanone, cyclohexenone, 2,6-dimethylcyclohexanone, cycloheptanone, cyclododecanone, acetylacetone, methylglyoxal and benzophenone.

Aldehydes which can be ised in the process of the invention subject to the abovementioned conditions are virtually all aliphatic and aromatic aldehydes. The aliphatic aldehydes can be linear, branched or cyclic, and can contain hetero atoms. The aldehydes can also bear substituents or contain functional groups which are inert under the conditions of the hydrogenative amination, for example alkoxy, alkenyloxy, alkylamino or dialkylamino groups, or may also be hydrogenated under the conditions of the hydrogenative amination, for example CC double or triple bonds. If polyfunctional aldehydes or keto aldehydes are to be aminated, amino alcohols, cyclic amines or multiply aminated products can be obtained by controlling the reaction conditions.

Preference is given to aminatively hydrogenating, for example, the following aldehydes:

formaldehyde, acetaldehyde, propionaldehyde, n-butyraldehyde, isobutyraldehyde, pivalalaldehyde, n-pentanal, n-hexanal, 2-ethylhexanal, 2-methylpentanal, 3-methylpentanal, 4-methylpentanal, glyoxal, benzaldehyde, p-methoxybenzaldehyde, p-methylbenzaldehyde, phenylacetaldehyde, (p-methoxyphenyl)acetaldehyde, (3,4-dimethoxyphenyl)acetaldehyde, 4-formyltetrahydropyran, 3-formyltetrahydrofuran, 5-formylvaleronitrile, citronellal, acrolein, methacrolein, ethylacrolein, citral, crotonaldehyde, 3-methoxypropionaldehyde, 3-aminopropionaldehyde, hydroxypivalalaldehyde, dimethylolpropionaldehyde, dimethylolbutyraldehyde, furfural, glyoxal, glutaraldehyde and also hydroformylated oligomers and polymers, e.g. hydroformylated polyisobutene (polyisobutene aldehyde) or the oligomer obtained by metathesis of 1-pentene and cyclopentene and hydroformylation.

As aminating agent in the hydrogenative amination of alcohols, aldehydes or ketones in the presence of hydrogen, it is possible to use either ammonia or primary or secondary, aliphatic or cycloaliphatic or aromatic amines.

When ammonia is used as aminating agent, the alcoholic hydroxyl group or the aldehyde group or the keto group is firstly converted into a primary amino group ($—NH_2$). The primary amine formed in this way can react with further alcohol or aldehyde or ketone to form the corresponding secondary amine and this can in turn react with further alcohol or aldehyde or ketone to form the corresponding, preferably symmetrical, tertiary amine. Depending on the composition of the reaction mixture or the feed stream (in the case of continuous operation) and depending on the reaction conditions employed, viz. pressure, temperature, reaction time (space velocity over the catalyst), primary, secondary or tertiary amines can be prepared preferentially as desired in this way.

Polyhydric alcohols or dialdehydes or oligoaldehydes or diketones or oligoketones or keto aldehydes can in this way be converted by intramolecular hydrogenative amination into cyclic amines such as pyrrolidines, piperidines, hexamethylenimines, piperazines and morpholines.

Primary or secondary amines can also be used like ammonia as aminating agents.

These aminating agents are preferably used for preparing unsymmetrically substituted dialkylamines or trialkylamines, e.g. ethyldiisopropylamine and ethyldicyclohexylamine. For example, the following monoalkylamines and dialkylamines are used as aminating agents: methylamine, dimethylamine, ethylamine, diethylamine, n-propylamine, di-n-propylamine, isopropylamine, diisopropylamine, isopropylethylamine, n-butylamine, di-n-butylamine, s-butylamine, di-s-butylamine, isobutylamine, n-pentylamine, s-pentylamine, isopentylamine, n-hexylamine, s-hexylamine, isohexylamine, cyclohexylamine, aniline, toluidine, piperidine, morpholine and pyrrolidine.

Amines which are particularly preferably prepared by the process of the invention are, for example, morpholine (from aminodiglycol), morpholine and/or bis(2-morpholinoethyl) ether (DMDEE) (from DEG and ammonia), 6-dimethylamino-1-hexanol-1 (from hexanediol and dimethylamine (DMA)), triethylamine (from ethanol and diethylamine (DEA)), dimethylethylamine (from ethanol and DMA), N—($C_{1-4}$-alkyl)morpholine (from DEG and mono($C_{1-4}$-alkyl)amine), N—($C_{1-4}$-alkyl)piperidine (from 1,5-pentanediol and mono($C_{1-4}$-alkyl)amine), piperazine (from aminoethylethanolamine (AEEA) and ammonia), N-methylpiperazine (from diethanolamine and MMA), N,N'-dimethylpiperazine (from N-methyldiethanolamine and MMA), ethylenediamine (EDA) and/or diethylenetriamine (DETA) and/or PIP (from monoethanolamine (MEOA) and ammonia), 2-ethylhexylamine and bis(2-ethylhexyl)amine (from 2-ethylhexanol and $NH_3$), tridecylamine and bis(tridecyl)amine (from tridecanol and $NH_3$), n-octylamine (from n-octanol and $NH_3$), 1,2-propylenediamine (from 2-hydroxypropylamine and $NH_3$), 1-diethylamino4-aminopentane (from 1-diethylamino4-hydroxypentane and $NH_3$), N,N-di ($C_{1-4}$-alkyl)cyclohexylamine (from cyclohexanone and/or cyclohexanol and di($C_{1-4}$-alkyl)amine), polyisobutenamine (from Pib-Oxo and $NH_3$), n-propylamines (e.g. mono-/dipropylamine, dimethylpropylamine) (from propionaldehyde and/or n-propanol and $NH_3$ or DMA), N,N-dimethyl-N-isopropylamine (from i-propanol and/or acetone and DMA), N,N-dimethyl-N-butylamines (1-butanol, 2-butanol or isobutanol and/or butanal, i-butanal or butanone and DMA), 2-(2-di($C_{1-4}$-alkyl)aminoethoxy)ethanol and/or bis(2-di($C_{1-4}$-alkyl)aminoethyl) ether (from DEG and di($C_{1-4}$-alkyl) amine), 1,2-ethylenediamine (EDA), diethylenetriamine (DETA) and/or piperazine (PIP) (from monoethylene glycol (MEG) and ammonia), 1,8-diamino-3,6-dioxaoctane and/or 1-amino-8-hydroxy-3,6-dioxaoctane (from triethylene glycol (TEG) and ammonia), 1-methoxy-2-propylamine (1-methoxyisopropylamine, MOIPA) (from 1-methoxy-2-propanol and ammonia).

EXAMPLES

Examples 1 to 8 below were carried out using a precipitated copper catalyst having the composition 55% by weight of CuO and 45% by weight of gamma-$Al_2O_3$ (after its last heat treatment and before it has been reduced by means of hydrogen). The catalyst was prepared using a method analogous to Example 1 of DE-A-24 45 303 and the catalyst was reduced at about 200° C. in a stream of hydrogen before commencement of the reaction.

1. Preparation of N,N-dimethylcyclohexylamine

Under atmospheric pressure (1 bar absolute), the fresh gas flow was set to a constant 100 standard l/h (standard l=standard liters=volume at STP) by means of hydrogen. Dimethylamine and cyclohexanone were vaporized separately and, after mixing, introduced into the hot fresh gas stream. The laden gas stream was reacted isothermally at 150° C. (+/−2° C.) and 1 bar absolute over the catalyst in a tube reactor. The synthesis was carried out at a space velocity over the catalyst of 0.10 $l_{alcohol}/l_{cat}\cdot h$, a molar ratio of dimethylamine/cyclohexanone of 3:1, an amount of circulating gas of 8.4 standard $m^3/h$ (standard $m^3$ =standard cubic meters=volume at STP) and an amount of fresh gas/$H_2$ of 100 standard liters/$l_{cat}\cdot h$. The cyclohexanone was completely reacted in the reaction and a selectivity of 88% based on the cyclohexanone used was achieved. The product was condensed in a water-cooled condenser and collected for purification by distillation.

2. Preparation of Piperidine

The pressure was set to a constant 20 bar (21 bar absolute), the fresh gas flow was set to a constant 300 standard l/h of hydrogen and the circulating gas was set to a constant approx. 400 pressure liters/($l_{cat}$·h). Ammonia and 1,5-pentanediol were vaporized separately and preheated alcohol was then introduced into the hot circulating gas stream, after which hot ammonia was fed into the reactor via a pressurized gas pump. The laden circulating gas stream was reacted isothermally at 220° C. (+/−2° C.) and 20 bar over the catalyst in the tube reactor. The synthesis was carried out at a space velocity over the catalyst of 0.20 $l_{alcohol}$/$l_{cat}$·h, a molar ratio of ammonia/pentanediol of 6:1 and an amount of fresh gas/$H_2$ of 300 standard liters/$l_{cat}$·h. The pentanediol was reacted completely in the reaction and a selectivity of 88-90% based on the pentanediol used was achieved. The product was condensed in a pressure gas separator and collected for purification by distillation.

3. Preparation of N-methylmorpholine

The pressure was set to a constant 20 bar (21 bar absolute), the fresh gas flow was set to a constant 300 standard l/h of hydrogen and the circulating gas was set to a constant approx. 400 pressure liters/($l_{cat}$·h). Monomethylamine and diethylene glycol were vaporized separately and preheated alcohol was then introduced into the hot circulating gas stream, after which hot monomethylamine was fed into the reactor via a pressurized gas pump. The laden circulating gas stream was reacted isothermally at 215° C. (+/−1° C.) and 20 bar over the catalyst in the tube reactor. The synthesis was carried out at a space velocity over the catalyst of 0.2-0.35 $l_{alcohol}$/$l_{cat}$·h, a molar ratio of ammonia/amine of 1:1.2-1.8 and an amount of fresh gas/$H_2$ of 300 standard liters/$l_{cat}$·h. The diethylene glycol was reacted completely in the reaction and a selectivity of 90% based on the diethylene glycol used was achieved. The product was condensed in a pressure gas separator and collected for purification by distillation.

4. Preparation of N-methylpiperidine

The pressure was set to a constant 20 bar (21 bar absolute), the fresh gas flow was set to a constant 300 standard l/h of hydrogen and the circulating gas was set to a constant approx. 400 pressure liters/($l_{cat}$·h). Monomethylamine and 1,5-pentanediol were vaporized separately and preheated alcohol was then introduced into the hot circulating gas stream, after which hot monomethylamine was fed into the reactor via a pressurized gas pump. The laden circulating gas stream was reacted isothermally at 205° C. (+/−2° C.) and 20 bar over the catalyst in the tube reactor. The synthesis was carried out at a space velocity over the catalyst of 0.2-0.5 $l_{alcohol}$/$l_{cat}$·h, a molar ratio of monomethylamine/pentanediol of 1.2-2.5:1 and an amount of fresh gas/$H_2$ of 300 standard liters/$l_{cat}$·h. The pentanediol was reacted completely in the reaction and a selectivity of 91-96% based on the pentanediol used was achieved. The product was condensed in a pressure gas separator and collected for purification by distillation.

5. Preparation of N,N-dimethylethylamine

The pressure was set to a constant 20 bar (21 bar absolute), the fresh gas flow was set to a constant 300 standard l/h of hydrogen and the circulating gas was set to a constant approx. 200 pressure liters/($l_{cat}$·h). Dimethylamine and ethanol were vaporized separately and preheated alcohol was then introduced into the hot circulating gas stream, after which hot dimethylamine was fed into the reactor via a pressurized gas pump. The laden circulating gas stream was reacted isothermally at 190° C. (+/−1° C.) and 20 bar over the catalyst in the tube reactor. The synthesis was carried out at a space velocity over the catalyst of 0.41 $l_{alcohol}$/$l_{cat}$·h, a molar ratio of ethanol/dimethylamine of 1.7:1 and an amount of fresh gas/$H_2$ of 300 standard liters/$l_{cat}$·h. The dimethylamine was reacted completely in the reaction and a selectivity of 94-97% based on the ethanol used was achieved. The product was condensed in a pressure gas separator and collected for purification by distillation.

6. Preparation of ethylpropylamine

The pressure was set to a constant 20 bar (21 bar absolute), the fresh gas flow was set to a constant 500 standard l/h of hydrogen and the circulating gas was set to a constant approx. 400 pressure liters/($l_{cat}$·h). Ethylamine and propanal were vaporized separately and preheated ethylamine was then introduced into the hot circulating gas stream, after which cold propanal was fed into the reactor via a static mixer just upstream of the reactor. The laden circulating gas stream was reacted isothermally at 120° C. (+/−3° C.) and 20 bar over the catalyst in the tube reactor. The synthesis was carried out at a space velocity over the catalyst of 0.15 $l_{propanal}$/$l_{cat}$·h, a molar ratio of propanal/ethylamine of 1:2.0 and an amount of fresh gas/$H_2$ of 500 standard liters/$l_{cat}$·h. The propanal was reacted completely in the reaction and a selectivity of>97% based on the propanal used was achieved. The product was condensed in a pressure gas separator and collected for purification by distillation.

7. Preparation of 2-(2-dimethylaminoethoxy)ethanol and bis(2-dimethylaminoethyl) Ether The pressure was set to a constant 20 bar (21 bar absolute), the fresh gas flow was set to a constant 300 standard l/h of hydrogen and the circulating gas was set to a constant approx. 400 pressure liters/($l_{cat}$·h). Dimethylamine and diethylene glycol were vaporized separately and preheated diethylene glycol was then introduced into the hot circulating gas stream, after which hot dimethylamine was fed into the reactor via a pressurized gas pump. The laden circulating gas stream was reacted isothermally at 190° C. (+/−1° C.) and 20 bar over the catalyst in the tube reactor. The synthesis was carried out at a space velocity over the catalyst of 0.2 $l_{alcohol}$/$l_{cat}$·h, a molar ratio of diethylene glycol/dimethylamine of 1:1.1 and an amount of fresh gas/$H_2$ of 300 standard liters/$l_{cat}$·h. 90% of the diethylene glycol was reacted in the reaction and a selectivity of 84% to 2-(2-dimethylaminoethoxy)ethanol and bis(2-dimethylaminoethyl) ether based on the diethylene glycol used was achieved. The product was condensed in a pressure gas separator and collected for purification by distillation.

8. Preparation of bis(2-morpholinoethyl) ether (=dimorpholinodiglycol)

The pressure was set to a constant 16 bar absolute, the fresh gas flow was set to a constant 300 standard l/h of hydrogen and the circulating gas was set to a constant approx. 300 pressure liters/($l_{cat}$·h). Ammonia and diethylene glycol were vaporized separately and preheated diethylene glycol was then introduced into the hot circulating gas stream, after which hot ammonia was fed into the reactor via a pressurized gas pump. The laden circulating gas stream was reacted isothermally at 210° C. (+/−2° C.) and 16 bar over the catalyst in the tube reactor. The synthesis was carried out at a space velocity over the catalyst of 0.30 $l_{alcohol}$/$l_{cat}$·h, a molar ratio of ammonia/alcohol of 3:1 and an amount of fresh gas/$H_2$ of 300 standard liters/$l_{cat}$·h. 90% of the alcohol was reacted in the reaction end a selectivity of 50% based on the diol used was achieved. The product was condensed in a pressure gas separator and collected for purification by distillation.

Examples 9 to 12 below were carried out using a copper catalyst having the composition 45% by weight of CuO, 45% by weight of gamma-$Al_2O_3$ and 10% by weight of NiO (after its last heat treatment and before it has been reduced by means of hydrogen).

The catalyst was prepared using a method analogous to Example 1 of EP-A-514 692 and the catalyst was reduced at about 200° C. in a stream of hydrogen before commencement of the reaction.

9. Preparation of Monoisopropylamine

Under atmospheric pressure (1 bar absolute), the fresh gas flow was set to a constant 500 standard l/h (standard l=standard liters=volume at STP) by means of hydrogen. Ammonia and acetone were vaporized separately and, after mixing, introduced into the hot fresh gas stream. The laden gas stream was reacted isothermally at 120° C. (+/−4° C.) and 20 bar absolute over the catalyst in a tube reactor. The synthesis was carried out at a space velocity over the catalyst of 0.40 $l_{alcohol}/l_{cat}$·h, a molar ratio of ammonia/acetone of 3:1, an amount of circulating gas of 4.2 standard $m^3$/h and an amount of fresh gas/$H_2$ of 500 standard liters/$l_{cat}$·h. The acetone was completely reacted in the reaction and a selectivity of 90% based on the cyclohexanone used was achieved. The product was condensed in a water-cooled condenser and collected for purification by distillation.

10. Preparation of Piperidine

The pressure was set to a constant 20 bar (21 bar absolute), the fresh gas flow was set to a constant 300 standard l/h of hydrogen and the circulating gas was set to a constant approx. 8.4 standard $m^3$/h. Ammonia and 1,5-pentanediol were vaporized separately and preheated alcohol was then introduced into the hot circulating gas stream, after which hot ammonia was fed into the reactor via a pressurized gas pump. The laden circulating gas stream was reacted isothermally at 210° C. (+/−2° C.) and 20 bar over the catalyst in the tube reactor. The synthesis was carried out at a space velocity over the catalyst of 0.40 $l_{alcohol}/l_{cat}$·h, a molar ratio of ammonia/pentanediol of 8:1 and an amount of fresh gas/$H_2$ of 300 standard liters/$l_{cat}$·h. The pentanediol was reacted completely in the reaction and a selectivity of 95% based on the pentanediol used was achieved. The product was condensed in a pressure gas separator and collected for purification by distillation.

11. Preparation of R-/S-MOIPA (racemate) (=1-methoxy-2-aminopropane)

The pressure was set to a constant 16 bar absolute, the fresh gas flow was set to a constant 300 standard l/h of hydrogen and the circulating gas was set to a constant approx. 400 pressure liters/($l_{cat}$·h). Ammonia and 1-methoxy-2-propanol were vaporized separately and preheated alcohol was then introduced into the hot circulating gas stream, after which hot ammonia was fed into the reactor via a pressurized gas pump. The laden circulating gas stream was reacted isothermally at 195° C. (+/−1° C.) and 16 bar over the catalyst in the tube reactor. The synthesis was carried out at a space velocity over the catalyst of 0.25 $l_{alcohol}/l_{cat}$·h, a molar ratio of ammonia/alcohol of 10:1 and an amount of fresh gas/$H_2$ of 300 standard liters/$l_{cat}$·h. 99.5%, i.e. virtually completely, of the alcohol was reacted in the reaction and a selectivity of 94% based on the alcohol used was achieved. The product was condensed in a pressure gas separator and collected for purification by distillation.

12. Preparation of Morpholine

The pressure was set to a constant 11 bar absolute, the fresh gas flow was set to a constant 200 standard l/h of hydrogen and the circulating gas was set to a constant approx. 400 pressure liters/($l_{cat}$·h). Ammonia and diethylene glycol were vaporized separately and preheated diethylene glycol was then introduced into the hot circulating gas stream, after which hot ammonia was fed into the reactor via a pressurized gas pump. The laden circulating gas stream was reacted isothermally at 210° C. (+/−2° C.) and 11 bar over the catalyst in the tube reactor. The synthesis was carried out at a space velocity over the catalyst of 0.30 $l_{alcohol}/l_{cat}$·h, a molar ratio of ammonia/alcohol of 10:1 and an amount of fresh gas/$H_2$ of 200 standard liters/$l_{cat}$·h. More than 97% of the alcohol was reacted in the reaction and a selectivity of greater than 97% based on the diol used was achieved. The product was condensed in a pressure gas separator and collected for purification by distillation.

The invention claimed is:

1. A process for the continuous preparation of an amine, the process comprising:

reacting an aldehyde and/or ketone with hydrogen and a nitrogen compound selected from the group consisting of ammonia, primary and secondary amines at a temperature in a range from 60 to 300° C. in the presence of a copper-containing catalyst, wherein a catalytically active composition of the catalyst prior to reduction with hydrogen comprises:

from 20 to 85% by weight of aluminum oxide ($Al_2O_3$), zirconium dioxide ($ZrO_2$), titanium dioxide ($TiO_2$) and/or silicon dioxide ($SiO_2$);

from 1 to 70% by weight of oxygen-containing compounds of copper, calculated as CuO;

from 0 to 50% by weight of oxygen-containing compounds of magnesium, calculated as MgO, oxygen-containing compounds of chromium, calculated as $Cr_2O_3$, oxygen-containing compounds of zinc, calculated as ZnO, oxygen-containing compounds of barium, calculated as BaO, and/or oxygen-containing compounds of calcium, calculated as CaO; and from 0 to 1% by weight of oxygen-containing compounds of nickel, calculated as NiO, based on the oxygen-containing compounds of copper, calculated as CuO, wherein the catalyst is prepared by coprecipitation of all the components, and the reaction is carried out isothermally in the gas phase in a tube reactor.

2. The process according to claim 1, wherein the reaction is carried out isothermally with a temperature fluctuation of not more than +/−8° C.

3. The process according to claim 1, wherein the reaction is carried out isothermally with a temperature fluctuation of not more than +/−5° C.

4. The process according to claim 1, wherein the reaction is carried out in a gas recycle mode in a tube reactor.

5. The process according to claim 4, wherein an amount of circulating gas is in a range from 40 to 1500 $m^3$ (at operating pressure)/[$m^3$ of catalyst (bed volume)·h].

6. The process according to claim 4, wherein an amount of circulating gas is in a range from 100 to 700 $m^3$ (at operating pressure)/[$m^3$ of catalyst (bed volume)·h].

7. The process according to claim 1, wherein the reaction is carried out in a shell-and-tube reactor or in a single-stream plant.

8. The process according to claim 1, wherein the reaction is carried out at an absolute pressure in a range from 1 to 300 bar.

9. The process according to claim 1, wherein the temperature in the reactor tube is controlled externally by an oil stream or a salt melt.

10. The process according to claim 1, wherein the circulating gas comprises at least 10% by volume of hydrogen ($H_2$).

11. The process according to claim 1, wherein a catalytically active composition of the catalyst prior to reduction with hydrogen comprises:

from 30 to 75% by weight of aluminum oxide ($Al_2O_3$), zirconium dioxide ($ZrO_2$), titanium dioxide ($TiO_2$) and/or silicon dioxide ($SiO_2$);

from 5 to 60% by weight of oxygen-containing compounds of copper, calculated as CuO; and from 0 to 20% by weight of oxygen-containing compounds of magnesium, calculated as MgO, oxygen-containing compounds of chromium, calculated as $Cr_2O_3$, oxygen-containing compounds of zinc, calculated as ZnO, oxygen-containing compounds of barium, calculated as BaO, and/or oxygen-containing compounds of calcium, calculated as CaO.

12. The process according to claim 1 for the preparation of N,N-di($C_{1-4}$-alkyl)cyclohexylamine by reacting cyclohexanone with di($C_{1-4}$-alkyl)amine.

13. The process according to claim 1 for the preparation of N,N-dimethyl-N-propylamine by reacting propanal with dimethylamine (DMA).

14. The process according to claim 1 for the preparation of N,N-dimethyl-N-isopropylamine by reacting acetone with DMA.

15. The process according to claim 1 for the preparation of N,N-dimethyl-N-(n-butyl)amine by reacting butanal with DMA.

16. The process according to claim 1 for the preparation of N,N-dimethyl-N-(isobutyl)amine by reacting i-butanal with DMA.

17. The process according to claim 1 for the preparation of N,N-dimethyl-N-(2-butyl)amine by reacting butanone with DMA.

18. The process according to claim 1 for the preparation of ethylpropylamine by reacting propanal with monoethylamine.

19. The process according to claim 1, wherein the nitrogen compound is added in a molar amount which is from 0.90 to 100 times that of the aldehyde and/or ketone used.

20. The process according to claim 1, wherein the nitrogen compound is added in a molar amount which is from 1.0 to 10 times that of the alcohol, aldehyde and/or ketone used.

21. The process according to claim 1, wherein the catalyst is present as a fixed bed in the reactor.

22. The process according to claim 1, wherein the aldehyde and/or ketone is/are added as an aqueous solution.

23. The process according to claim 1, wherein the ammonia or the primary or secondary amine is added as an aqueous solution.

* * * * *